(12) United States Patent
Utima et al.

(10) Patent No.: US 11,648,190 B2
(45) Date of Patent: May 16, 2023

(54) TOOTHPASTES CONTAINING CALCIUM CARBONATE, XANTHAN GUM AND POLYACRYLIC ACID POLYMER

(71) Applicant: Colgate-Palmolive Company, New York, NY (US)

(72) Inventors: Enzo Utima, Sao Paulo (BR); Erico Prat, San Paulo (BR); Abraham Cazes, Edo Mex C.P. (MX); Paulo Focassio, Sao Paulo (BR); Murilo Nogueira Nakajima, Sao Paulo (BR)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 17/249,588

(22) Filed: Mar. 5, 2021

(65) Prior Publication Data

US 2021/0275413 A1    Sep. 9, 2021

Related U.S. Application Data

(60) Provisional application No. 62/985,990, filed on Mar. 6, 2020.

(51) Int. Cl.
| | | |
|---|---|---|
| *A61K 8/21* | (2006.01) | |
| *A61K 8/04* | (2006.01) | |
| *A61K 8/24* | (2006.01) | |
| *A61K 8/27* | (2006.01) | |
| *A61K 8/34* | (2006.01) | |
| *A61K 8/44* | (2006.01) | |
| *A61K 8/46* | (2006.01) | |
| *A61K 8/73* | (2006.01) | |
| *A61K 8/81* | (2006.01) | |
| *A61K 8/86* | (2006.01) | |
| *A61Q 11/00* | (2006.01) | |

(52) U.S. Cl.
CPC ............... *A61K 8/21* (2013.01); *A61K 8/042* (2013.01); *A61K 8/24* (2013.01); *A61K 8/27* (2013.01); *A61K 8/345* (2013.01); *A61K 8/347* (2013.01); *A61K 8/44* (2013.01); *A61K 8/463* (2013.01); *A61K 8/73* (2013.01); *A61K 8/8147* (2013.01); *A61K 8/86* (2013.01); *A61Q 11/00* (2013.01); *A61K 2800/28* (2013.01); *A61K 2800/48* (2013.01); *A61K 2800/594* (2013.01); *A61K 2800/92* (2013.01)

(58) Field of Classification Search
CPC .. A61K 8/81; A46B 9/04; A61C 17/00; A61Q 11/00
USPC ................................. 424/49, 52, 55; 433/216
IPC ......................................................... A61Q 11/00
See application file for complete search history.

(56) References Cited

U.S. PATENT DOCUMENTS

| | | | |
|---|---|---|---|
| 8,623,333 B2 | 1/2014 | Crawshaw et al. | |
| 9,949,907 B2 | 4/2018 | D'Ambrogio | |
| 10,596,082 B2 | 3/2020 | Utima et al. | |
| 2004/0191187 A1 | 9/2004 | Luo et al. | |
| 2012/0288455 A1* | 11/2012 | Pilch .................. | A61Q 11/00 424/49 |
| 2015/0297477 A1* | 10/2015 | Poth .................... | A61K 8/21 424/52 |

FOREIGN PATENT DOCUMENTS

| | | |
|---|---|---|
| FR | 2755010 | 4/1998 |
| WO | 2012/087325 | 6/2012 |
| WO | 2015/094154 | 6/2015 |

OTHER PUBLICATIONS

Kuchenmeister et al., "How much squeezing powder is required to get the toothpaste out of the tube? Yield stress determination using the HAAKE Viscotester iQ." thermoscientific.com/mc, published online 2016 copyright Feb. 2014 (Year: 2016).*

International Search Report and the Written Opinion of the International Searching Authority issued in International Application PCT/US2021/070241 dated Jun. 23, 2021.

* cited by examiner

*Primary Examiner* — Walter E Webb

(57) ABSTRACT

The present invention provides calcium carbonate-based oral care compositions, in particular toothpastes comprising a thickening system comprising 0.2-0.5 wt. % xanthan gum and 0.2-0.5 wt. % synthetic polyacrylic acid polymer, as well as methods of using these compositions.

9 Claims, No Drawings

TOOTHPASTES CONTAINING CALCIUM CARBONATE, XANTHAN GUM AND POLYACRYLIC ACID POLYMER

CROSS REFERENCE TO RELATED APPLICATIONS

This application claims the benefit and priority of U.S. provisional application 62/985,990, filed on Mar. 6, 2020.

BACKGROUND

Calcium carbonate abrasives are commonly used in toothpastes but require a suitable binder to provide a paste formulation having good viscosity and mouthfeel. Current calcium carbonate-based anti-cavity toothpastes typically utilize a high concentration of calcium carbonate abrasive, combined with either single or dual gum systems to provide targeted therapeutic benefits and product physical stability. Current gum systems for oral care compositions are basically restricted to carboxymethylcellulose (CMC), xanthan gum and carrageenan. Each polymer provides the formula with different rheological properties. The best choice depends on the formulation (compatibility/stability), manufacturing process and cost requirements.

It would be desirable to provide more cost-effective calcium carbonate-based anti-cavity toothpastes which have improved rheology profile, aesthetics and mouthfeel.

BRIEF SUMMARY

In one aspect, the invention provides an oral care composition, e.g., toothpaste or gel, which comprises a calcium carbonate and a thickening system comprising xanthan gum and a synthetic polyacrylic acid polymer, wherein the calcium carbonate is present in an amount of from 25% to 40% by weight of the composition, wherein xanthan gum is present in an amount of 0.2% to 0.5% by weight of the composition, and wherein the synthetic polyacrylic acid polymer is present in an amount of from 0.2% to 0.5% by weight of the composition. In some embodiments, the calcium carbonate is natural calcium carbonate, precipitated calcium carbonate or a combination thereof. In some embodiments, the calcium carbonate is precipitated calcium carbonate. In some embodiments, the synthetic polyacrylic acid polymer is a carbomer. In some embodiments, the synthetic polyacrylic acid polymer is selected from Carbopol® 956, Carbopol® ETD2020 and a combination thereof. In some embodiments, the calcium carbonate is precipitated calcium carbonate. In certain embodiments, the synthetic polyacrylic acid polymer is Carbopol® 956. In certain embodiments, the synthetic polyacrylic acid polymer is a combination of Carbopol® 956 and Carbopol® ETD2020.

In another aspect, the invention provides a method comprising applying an effective amount of any of oral care compositions as disclosed herein to the oral cavity, e.g., by brushing, to a subject in need thereof, to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity.

In another aspect, the invention provides the use of a thickening system comprising xanthan gum and a synthetic polyacrylic acid polymer in the manufacture of an oral care composition, e.g., toothpaste or gel, comprising a calcium carbonate, wherein the calcium carbonate is present in an amount of from 25% to 40% by weight of the composition, wherein xanthan gum is present in an amount of 0.2% to 0.5% by weight of the composition, and wherein the synthetic polyacrylic acid polymer is present in an amount of from 0.2% to 0.5% by weight of the composition. In some embodiments, the calcium carbonate is natural calcium carbonate, precipitated calcium carbonate or a combination thereof. In some embodiments, the calcium carbonate is precipitated calcium carbonate. In some embodiments, the synthetic polyacrylic acid polymer is selected from Carbopol® 956, Carbopol® ETD2020 and a combination thereof. In certain embodiments, the synthetic polyacrylic acid polymer is Carbopol® 956. In certain embodiments, the synthetic polyacrylic acid polymer is a combination of Carbopol® 956 and Carbopol® ETD2020.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight. The amounts given are based on the active weight of the material.

The present inventors have found that calcium carbonate-based oral care compositions with acceptable rheological properties can be obtained by formulating the compositions with specific amounts of xanthan gum and a synthetic polyacrylic acid polymer (e.g., Carbopol® 956). It has been found that viscosity, yield stress and pressure are kept flat overtime in PCC (precipitated calcium carbonate)-based oral care compositions with the Carbopol-xanthan gum system. Furthermore, it has been found that acceptable rheological properties and stand up can be achieved at a low level of carbomer (e.g., 0.4%). Thus, the use of a thickening system comprising a synthetic polyacrylic acid polymer and xanthan gum allows more cost-effective calcium carbonate-based anti-cavity toothpastes which have improved rheology profile, aesthetics and mouthfeel.

The present invention provides, in an aspect, an oral care composition (Compositions 1.0), e.g., toothpaste or gel, which comprises a calcium carbonate and a thickening system comprising xanthan gum and a synthetic polyacrylic acid polymer, wherein the calcium carbonate is present in an amount of from 25% to 40% by weight of the composition, wherein xanthan gum is present in an amount of 0.2% to 0.5% by weight of the composition, and wherein the synthetic polyacrylic acid polymer is present in an amount of from 0.2% to 0.5% by weight of the composition.

For example, the invention includes:

1.1. Composition 1.0, wherein the calcium carbonate is natural calcium carbonate, precipitated calcium carbonate or a combination thereof.
1.2. Any of the preceding compositions, wherein the calcium carbonate is precipitated calcium carbonate.
1.3. Any of the preceding compositions, wherein the calcium carbonate is present in an amount of from 25% to 35%, from 30% to 40%, from 35% to 40%, from 30% to 35%, from 32% to 38%, from 33% to 37%, from 34% to 36%, or about 35% by weight of the composition.
1.4. Any of the preceding compositions, wherein the synthetic polyacrylic acid polymer is a carbomer.
1.5. Any of the preceding compositions, wherein the synthetic polyacrylic acid polymer is selected from Carbopol® 956, Carbopol® ETD2020 and a combination thereof.
1.6. Any of the preceding compositions, wherein the synthetic polyacrylic acid polymer is Carbopol® 956.
1.7. Any of the preceding compositions, wherein the synthetic polyacrylic acid polymer is Carbopol® ETD2020.
1.8. Any of the preceding compositions, wherein the synthetic polyacrylic acid polymer is a combination of Carbopol® 956 and Carbopol® ETD2020.
1.9. Any of the preceding compositions, wherein the synthetic polyacrylic acid polymer is present in an amount of from 0.2% to 0.4%, from 0.3% to 0.5%, from 0.35% to 0.45%, e.g., about 0.3% or about 0.4%, by weight of the composition.
1.10. Any of the preceding compositions, wherein xanthan gum is present in an amount of from 0.2% to 0.4%, from 0.3% to 0.5%, from 0.35% to 0.45%, e.g., about 0.3% or about 0.4%, by weight of the composition.
1.11. Any of the preceding compositions, wherein the thickening system consists of xanthan gum and a synthetic polyacrylic acid polymer, i.e., the composition does not contain any additional thickening agent other than xanthan gum and the synthetic polyacrylic acid polymer.
1.12. Any of the preceding compositions, wherein the composition comprises a basic amino acid.
1.13. Any of the preceding compositions, wherein the basic amino acid comprises one or more of arginine, lysine, citrulline, ornithine, creatine, histidine, diaminobutanoic acid, diaminopropionic acid, salts thereof, or combinations thereof.
1.14. Any of the preceding compositions, wherein the basic amino acid has the L-configuration.
1.15. Any of the preceding compositions, wherein the basic amino acid is present in an amount of from 1% to 15%, e.g., from 1% to 10%, from 1% to 5%, from 1% to 3%, from 1% to 2%, from 1.2% to 1.8%, from 1.4% to 1.6%, or about 1.5% by weight of the composition, being calculated as free base form.
1.16. Any of the preceding compositions, wherein the basic amino acid comprises arginine.
1.17. Any of the preceding compositions, wherein the basic amino acid comprises L-arginine.
1.18. Any of the preceding compositions, wherein the basic amino acid comprises arginine bicarbonate, arginine phosphate, arginine sulfate, arginine hydrochloride or combinations thereof, optionally wherein the basic amino acid is arginine bicarbonate.
1.19. Any of the preceding compositions, wherein the composition comprises a zinc ion source.
1.20. Any of the preceding compositions, wherein the zinc ion source is selected from the group consisting of zinc oxide, zinc sulfate, zinc chloride, zinc citrate, zinc lactate, zinc gluconate, zinc malate, zinc tartrate, zinc carbonate, zinc phosphate and a combination thereof
1.21. Any of the preceding compositions, wherein the zinc ion source is present in an amount of from 0.01% to 5%, e.g., 0.1% to 4%, or 0.5% to 3%, by weight of the composition.
1.22. Any of the preceding compositions, wherein the zinc ion source is selected from the group consisting of zinc oxide, zinc citrate, and a combination thereof, optionally wherein the zinc ion source is a combination of zinc oxide and zinc citrate.
1.23. Any of the preceding compositions, wherein zinc oxide is present in an amount of 0.5% to 2%, e.g., 0.5% to 1.5%, or about 1% by weight of the composition.
1.24. Any of the preceding compositions, wherein zinc citrate is present in an amount of 0.1% to 2.5%, 0.1% to 2%, 0.1% to 1%, 0.25 to 0.75%, 1.5% to 2.5%, about 2%, or about 0.5% by weight of the composition.
1.25. Any of the preceding compositions, wherein the composition comprises a fluoride ion source.
1.26. Any of the preceding compositions, wherein the fluoride ion source is selected from sodium fluoride, stannous fluoride, potassium fluoride, sodium monofluorophosphate, sodium fluorosilicate, ammonium fluorosilicate, amine fluoride (e.g., N'-octadecyltrimethylendi amine-N,N,N'-tris(2-ethanol)-dihydrofluoride), ammonium fluoride, titanium fluoride, hexafluorosulfate, and a combination thereof
1.27. Any of the preceding compositions, wherein the fluoride ion source is present in an amount sufficient to supply 25 ppm to 5,000 ppm of fluoride ions, generally at least 500 ppm, e.g., 500 to 2000 ppm, e.g., 1000 ppm to 1600 ppm, e.g., 1450 ppm.
1.28. Any of the preceding compositions, wherein the fluoride ion source is sodium fluoride.
1.29. Any of the preceding compositions, wherein the composition comprises a potassium ion source.
1.30. Any of the preceding compositions, wherein the potassium ion source is selected from the group consisting of potassium citrate, potassium tartrate, potassium chloride, potassium sulfate, potassium nitrate and a combination thereof
1.31. Any of the preceding compositions, wherein the potassium ion source is present in an amount of from 0.1% to 5.5%, e.g., from 0.1% to 4%, or from 0.5% to 3%, by weight of the composition.
1.32. Any of the preceding compositions, wherein the composition does not comprise any additional abrasive other than calcium carbonate.
1.33. Any of the preceding compositions, wherein the composition comprises an additional abrasive other than calcium carbonate.
1.34. Any of the preceding compositions, wherein the additional abrasive is selected from silica abrasives, calcium phosphate abrasives, e.g., tricalcium phosphate ($Ca_3(PO_4)_2$), hydroxyapatite ($Ca_{10}(PO_4)_6(OH)_2$), or dicalcium phosphate dihydrate ($CaHPO_4 \cdot 2H_2O$, also sometimes referred to herein as DiCal) or calcium pyrophosphate; or abrasives such as sodium metaphosphate, potassium metaphosphate, aluminum silicate, calcined alumina, bentonite or other siliceous materials, and combinations thereof.

1.35. Any of the preceding compositions, wherein the additional abrasive comprises a silica abrasive.

1.36. Any of the preceding compositions, wherein the composition comprises a humectant, optionally wherein the humectant is selected from sorbitol, glycerin and a mixture thereof 1.37. Any of the preceding compositions, wherein the humectant comprises glycerin, optionally wherein glycerin is present in an amount of from 10% to 40%, from 15% to 30%, from 15% to 25%, or about 20% by weight of the composition.

1.38. Any of the preceding compositions, wherein the humectant comprises sorbitol, optionally wherein sorbitol is present in an amount of from 10% to 40%, from 15% to 30%, from 15% to 25%, or about 20% by weight of the composition.

1.39. Any of the preceding compositions, wherein the composition comprises one or more soluble phosphate salts, e.g., selected from tetrasodium pyrophosphate (TSPP), sodium tripolyphosphate (STPP) and a combination thereof 1.40. Any of the preceding compositions, wherein the composition comprises water, optionally wherein water is present in an amount of from 10% to 80%, from 20% to 60%, from 20% to 40%, from 10% to 30%, from 20% to 30% or from 25% to 35% by weight of the composition.

1.41. Any of the preceding compositions, wherein composition comprises one or more surfactants, e.g., selected from anionic, cationic, zwitterionic, and nonionic surfactants, and mixtures thereof.

1.42. Any of the preceding compositions, wherein the composition comprises an anionic surfactant, e.g., a surfactant selected from sodium lauryl sulfate, sodium ether lauryl sulfate, and mixtures thereof, e.g., in an amount of from about 0.3% to about 4.5% by weight, e.g., 1-2% sodium lauryl sulfate (SLS) by weight of the composition.

1.43. Any of the preceding compositions, wherein the composition comprises a zwitterionic surfactant, for example a betaine surfactant, for example cocamidopropyl betaine, e.g., in an amount of 0.1%-4.5% by weight, e.g., 0.5-2% cocamidopropyl betaine by weight of the composition.

1.44. Any of the preceding compositions, wherein the composition comprises a nonionic surfactant, e.g., a poly(propylene oxide)/poly(ethylene oxide) copolymer.

1.45. Any of the preceding compositions, wherein the composition comprises:
   a carbomer in an amount of from 0.2% to 0.5% (e.g., about 0.4%),
   xanthan gum in an amount of from 0.2% to 0.5% (e.g., about 0.4%),
   glycerin in an amount of 15% to 30% (e.g., about 20%), and
   precipitated calcium carbonate (PCC) in an amount of from 25% to 40% (e.g., about 35%) by weight of the composition.

1.46. Any of the preceding compositions, wherein the composition further comprises a polyethylene glycol (e.g., PEG 600) in an amount of less than or equal to 1%, e.g., from 0.01 to 1%, or from 0.1% to 1%, by weight of the composition.

1.47. Any of the preceding compositions, wherein the composition is a toothpaste or gel.

1.48. Any of the preceding compositions, wherein the composition is a toothpaste.

1.49. Any of the preceding compositions, wherein the composition exhibits a viscosity of 200000-1000000 cps and a dynamic yield stress of 60-250 Pa.

1.50. Any of the preceding compositions for use in (i) reducing or inhibiting formation of dental caries, (ii) reducing, repairing or inhibiting pre-carious lesions of the enamel, (iii) reducing or inhibiting demineralization and promote remineralization of the teeth, (iv) reducing hypersensitivity of the teeth, (v) reducing or inhibiting gingivitis, (vi) promoting healing of sores or cuts in the oral cavity, (vii) reducing levels of acid producing bacteria, (viii) reducing or inhibiting microbial biofilm formation in the oral cavity, (ix) reducing or inhibiting plaque formation in the oral cavity, (x) promoting systemic health, or (xi) cleaning teeth and oral cavity.

The oral care composition of the invention may be a toothpaste or gel. In some embodiments, the oral care composition is a toothpaste. The oral care composition may be a single phase oral care composition. For example, all the components of the oral care composition may be maintained together with one another in a single phase and/or vessel. For example, all the components of the oral care composition may be maintained in a single phase, such as a single homogenous phase. In another embodiment, the oral care composition may be a multi-phase oral care composition.

The oral care composition of the invention may contain an orally acceptable carrier. As used herein, an "orally acceptable carrier" refers to a material or combination of materials that are safe for use in the compositions of the invention, commensurate with a reasonable benefit/risk ratio. Such materials include but are not limited to, for example, water, humectants, ionic active ingredients, buffering agents, anti-calculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof. Such materials are well known in the art and are readily chosen by one skilled in the art based on the physical and aesthetic properties desired for the compositions being prepared. In some embodiment, the orally acceptable carrier may include an orally acceptable solvent. Illustrative solvents may include, but are not limited to, one or more of ethanol, phenoxyethanol, isopropanol, water, cyclohexane, methyl glycol acetate, benzyl alcohol, or the like, or any mixture or combination thereof. In a particular embodiment, the orally acceptable solvent includes benzyl alcohol.

Water may be present in the oral compositions of the invention. Water employed in the preparation of commercial oral compositions should be deionized and free of organic impurities. Water commonly makes up the balance of the compositions and includes about 10% to about 80%, about 20% to about 60%, about 20% to 40%, about 10% to about 30%, about 20% to 30%, or about 25% to 35% by weight of the oral compositions. This amount of water includes the free water which is added plus that amount which is introduced with other materials such as with sorbitol or any components of the invention.

The oral care composition of the invention comprises a calcium carbonate in an amount of from 25% to 40% by weight of the composition. In some embodiments, the calcium carbonate is present in an amount of from 25% to 35%, from 30% to 40%, from 35% to 40%, from 30% to 35%, from 32% to 38%, from 33% to 37%, from 34% to 36%, or about 35% by weight of the composition. The calcium carbonate may be natural calcium carbonate, precipitated calcium carbonate or a combination thereof. In some embodiments, the calcium carbonate is precipitated calcium carbonate. In some embodiments, the calcium carbonate may have a particle size or D50 of less than or equal to about 10 μm, less than or equal to about 8 μm, less than or equal to about 5 μm, or less than or equal to about 3 μm. The calcium carbonate may have a particle size or D50 of greater than or equal to about 0.01 μm, greater than or equal to about 0.05 μm, greater than or equal to about 0.1 μm, greater than or equal to about 0.5 μm, or greater than or equal to about 1 μm.

In some embodiments, the composition does not contain any additional abrasive other than calcium carbonate.

In some embodiments, the oral care composition of the invention comprises an additional abrasive other than calcium carbonate. As used herein, the term "abrasive" may also refer to materials commonly referred to as "polishing agents". Any orally acceptable abrasive may be used, but preferably, type, fineness (particle size), and amount of the abrasive may be selected such that the tooth enamel is not excessively abraded in normal use of the oral care composition. The abrasives may have a particle size or D50 of less than or equal to about 10 μm, less than or equal to about 8 μm, less than or equal to about 5 μm, or less than or equal to about 3 μm. The abrasives may have a particle size or D50 of greater than or equal to about 0.01 μm, greater than or equal to about 0.05 μm, greater than or equal to about 0.1 μm, greater than or equal to about 0.5 μm, or greater than or equal to about 1 μm. Illustrative abrasives may include, but are not limited to, metaphosphate compounds, phosphate salts (e.g., insoluble phosphate salts), such as sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate, magnesium carbonate, hydrated alumina, silica, zirconium silicate, aluminum silicate including calcined aluminum silicate, polymethyl methacrylate, or the like, or mixtures and combinations thereof. In some embodiments, the additional abrasive is a silica abrasive.

The oral care composition of the invention comprises xanthan gum in an amount of 0.2-0.5% by weight of the composition. In some embodiments, xanthan gum is present in an amount of from 0.2% to 0.4%, from 0.3% to 0.5%, from 0.35% to 0.45%, e.g., about 0.3% or about 0.4%, by weight of the composition.

The oral care composition of the invention comprises a synthetic polyacrylic acid polymer in an amount of 0.2-0.5% by weight of the composition. In some embodiments, the synthetic polyacrylic acid polymer is present in an amount of from 0.2% to 0.4%, from 0.3% to 0.5%, from 0.35% to 0.45%, e.g., about 0.3% or about 0.4%, by weight of the composition. In some embodiments, the synthetic polyacrylic polymer is a carbomer. Carbomers are synthetic high-molecular-weight polyacrylic acids cross-linked with allyl sucrose or allyl pentaerythritol and contain between 56 and 68% w/w carboxylic acid groups. Non-limiting examples of carbomers can include carbomer 934, carbomer 934P, carbomer 940, carbomer 94, carbomer 1342, carbomer copolymers, carbomer homopolymers, carbomer interpolymers, and combinations thereof. Some carbomers are available commercially as from B. F. Goodrich as the Carbopol® series. Particularly preferred Carbopols include Carbopol® 934, 940, 941, 956, 974P, ETD2020 and mixtures thereof. In some embodiments, the synthetic polyacrylic acid polymer is selected from Carbopol® 956, Carbopol® ETD2020 and a combination thereof. In some embodiments, the synthetic polyacrylic acid polymer is Carbopol® 956. In some embodiments, the synthetic polyacrylic acid polymer is Carbopol® ETD2020. In some embodiments, the synthetic polyacrylic acid polymer is a combination of Carbopol® 956 and Carbopol® ETD2020.

In some embodiments, the oral care composition of the invention may contain an additional thickening agent other than xanthan gum and a synthetic polyacrylic acid polymer. As used herein, the term "thickening agents" refers to agents that are used to control the viscosity of the oral care composition. Illustrative thickeners may be or include, but are not limited to, colloidal silica, fumed silica, a cross-linked polyvinylpyrrolidone (PVP) polymer, cross-linked polyvinylpyrrolidone (PVP), or the like, or mixtures or combinations thereof. In some embodiments, the thickening system includes a cross-linked polyvinylpyrrolidone (PVP) polymer. The thickening system may also include POLY-PLASDONE® XL 10F, which is commercially available from Ashland Inc. of Covington, Ky. Illustrative thickeners may also be or include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, gum arabic, and tragacanth), colloidal magnesium aluminum silicate, or the like, or mixtures or combinations thereof.

In some embodiments, the oral care composition does not contain any additional thickening agent other than xanthan gum and a synthetic polyacrylic acid polymer.

In some embodiments, the oral care composition of the invention may exhibit a viscosity of 200000-1000000 cps and a dynamic yield stress of 60-250 Pa. Rheological properties such as viscosity and dynamic yield stress of the composition may be measured by methods known in the art. For example, viscosity and dynamic yield stress of the composition may be measured at room temperature by Brookfield viscometer using the V74 spindle flow method, equipped with a software, e.g., Fitflow software, which calculates dynamic yield stress from measured rheological data. For example, dynamic yield stress may be calculated using the Herschel-Bulkley (HB) Model.

The oral care composition of the invention may include fluoride, such as one or more fluoride ion sources (e.g., soluble fluoride salts). A wide variety of fluoride ion-yielding materials may be employed as sources of soluble fluoride. Illustrative fluoride ion sources include, but are not limited to, sodium fluoride, stannous fluoride, potassium fluoride, sodium monofluorophosphate, fluorosilicate salts, such as sodium fluorosilicate and ammonium fluorosilicate, amine fluoride, ammonium fluoride, and combinations thereof. In some embodiment, the fluoride ion source includes sodium fluoride. The amount of the fluoride ion source present in the oral care composition may be greater than 0 weight % and less than 0.8 wt. %, less than 0.7 wt. %, less than 0.6 wt. %, less than 0.5 wt. %, or less than 0.4 wt. %. The fluoride ion sources may be present in an amount sufficient to supply 25 ppm to 5,000 ppm of fluoride ions, generally at least 500 ppm, e.g., 500 to 2000 ppm, e.g., 1000 ppm to 1600 ppm, e.g., 1450 ppm.

The oral care composition of the invention may comprise a basic amino acid in free or salt form. The basic amino acids which can be used in the compositions include not only naturally occurring basic amino acids, such as arginine, lysine, and histidine, but also any basic amino acids having a carboxyl group and an amino group in the molecule, which are water-soluble and provide an aqueous solution with a pH of about 7 or greater. Accordingly, basic amino acids include, but are not limited to, arginine, lysine, citrulline ornithine, creatine, histidine, diaminobutanoic acid, diaminopropionic acid, salts thereof or combinations thereof. In a particular embodiment, the basic amino acids are selected from arginine, lysine, citrulline, and ornithine. The basic amino acids of the oral care composition may generally be present in the L-form or L-configuration. The basic amino acids may be provided as a salt of a di- or tri-peptide including the amino acid. In some embodiments, at least a portion of the basic amino acid present in the oral care composition is in the salt form. In some embodiments, the basic amino acid is arginine, for example, L-arginine, or a salt thereof. Arginine may be provided as free arginine or a salt thereof. For example, Arginine may be provided as arginine phosphate, arginine hydrochloride, arginine sulfate, arginine bicarbonate, or the like, and mixtures or combinations thereof. The basic amino acid may be provided as a solution or a solid. For example, the basic amino acid may be provided as an aqueous solution. In some embodiment, the amino acid includes or is provided by an arginine bicarbonate solution. For example, the amino acid may be provided by an about 40% solution of the basic amino acid, such as arginine bicarbonate or alternatively called as arginine carbamate. In some embodiments, the basic amino acid is present in an amount of from 1% to 15%, e.g., from 1% to 10%, from 1% to 5%, from 1% to 3%, from 1% to 2%, from 1.2% to 1.8%, from 1.4% to 1.6%, or about 1.5% by weight of the composition, being calculated as free base form.

The oral care composition of the invention may comprise a zinc ion source. The zinc ion source may be or include a zinc ion and/or one or more zinc salts. For example, the zinc salts may at least partially dissociate in an aqueous solution to produce zinc ions. Illustrative zinc salts may include, but are not limited to, zinc lactate, zinc oxide, zinc chloride, zinc phosphate, zinc citrate, zinc acetate, zinc borate, zinc butyrate, zinc carbonate, zinc formate, zinc gluconate, zinc glycerate, zinc glycolate, zinc picolinate, zinc propionate, zinc salicylate, zinc silicate, zinc stearate, zinc tartrate, zinc undecylenate, and mixtures thereof. In some embodiments, the zinc ion source is present in an amount of from 0.01% to 5%, e.g., 0.1% to 4%, or 1% to 3%, by weight of the composition.

In some embodiments, the zinc ion source is selected from zinc oxide, zinc citrate, and a combination thereof. Zinc oxide may be present in an amount of 0.5% to 2%, e.g., 0.5% to 1.5%, or about 1% by weight of the composition. Zinc citrate may be present in an amount of 0.1% to 1%, 0.25% to 0.75%, about 0.5% by weight of the composition. In some embodiments, the composition comprises zinc oxide and zinc citrate. The composition may comprise zinc oxide in an amount of 0.5% to 2%, e.g., 0.5% to 1.5%, about 1% or about 1.2% by weight of the composition and zinc citrate in an amount of 0.1% to 2.5%, 0.1% to 2%, 0.1% to 1%, 0.25 to 0.75%, 1.5% to 2.5%, about 2%, or about 0.5% by weight of the composition. In certain embodiments, the composition comprises zinc oxide in an amount of about 1% by weight of the composition and zinc citrate in an amount of about 0.5% by weight of the composition.

The oral care composition of the invention may comprise an orally acceptable desensitizing, or tooth sensitivity protecting, agent. Suitable desensitizing agents include without limitation potassium salts such as potassium citrate, potassium tartrate, potassium chloride, potassium sulfate and potassium nitrate. Another suitable desensitizing agent is sodium nitrate. Alternatively or in addition, the composition may comprise a local or systemic analgesic such as aspirin, codeine, acetaminophen, sodium salicylate or triethanolamine salicylate. One or more desensitizing agents and/or analgesics may be present in a desensitizing and/or analgesic effective amount of typically from 0.01% to 5.5%, for example, from 0.1% to 4%, from 0.1% to 3% or from 0.5% to 3%, by weight, of the composition.

The oral care composition of the present invention may include at least one surfactant or solubilizer. Suitable surfactants include neutral surfactants (such as polyoxyethylene hydrogenated castor oil or fatty acids of sugars), anionic surfactants (such as sodium lauryl sulfate), cationic surfactants (such as the ammonium cation surfactants) or zwitterionic surfactants. These surfactants or solubilizers may be present in amounts of typically from 0.01% to 5%, from 0.01% to 2%; or from 1% to 2%; or about 1.5%, by weight of the composition. In some embodiments, the composition may comprise an anionic surfactant. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium lauryl ether sulfate, ammonium lauryl sulfate, ammonium lauryl ether sulfate, sodium cocoyl monoglyceride sulfonate, sodium lauryl sarcosinate, sodium lauryl isoethionate, sodium laureth carboxylase, and sodium dodecyl benzenesulfonate. In some embodiments, the anionic surfactant, e.g., sodium lauryl sulfate (SLS), is present in an amount of from about 0.3% to about 4.5% by weight, e.g., 1-2% by weight of the composition. In some embodiments, the composition may comprise a betaine zwitterionic surfactant. The betaine zwitterionic surfactant may be a $C_8-C_{16}$ aminopropyl betaine, e.g., cocamidopropyl betaine. In some embodiments, the betaine zwitterionic surfactant, e.g., cocamidopropyl betaine, is present in an amount of from 1% to 1.5%, from 1.1% to 1.4%, from 1.2% to 1.3%, or about 1.25% by weight of the composition. In some embodiments, the composition may comprise a non-ionic block copolymer. The non-ionic block copolymer may be a poly(propylene oxide)/poly(ethylene oxide) copolymer. In some embodiments, the copolymer has a polyoxypropylene molecular mass of from 3000 to 5000 g/mol and a polyoxyethylene content of from 60 to 80 mol %. In some embodiments, the non-ionic block copolymer is a poloxamer. In some embodiments, the non-ionic block copolymer is selected from: Poloxamer 338, Poloxamer 407, Poloxamer, 237, Poloxamer, 217, Poloxamer 124, Poloxamer 184, Poloxamer 185, and a combination of two or more thereof.

The oral care compositions of the invention may include one or more humectants. Humectants can reduce evaporation and also contribute towards preservation by lowering water activity and can also impart desirable sweetness or flavor to compositions. Illustrative humectants may be or include, but are not limited to, glycerin, propylene glycol, polyethylene glycol, sorbitol, xylitol, or the like, or any mixture or combination thereof. In a preferred embodiment, the orally acceptable vehicle may be or include, but is not limited to, glycerin or sorbitol. In some embodiments, the humectant is selected from glycerin, sorbitol and a combination thereof. In some embodiments, the humectant may be present in an amount of from 20% to 60%, for example from 15% to 40%, from 15% to 35%, from 20% to 40%, from 30% to 50%, from 30% to 40%, or from 40% to 45%, by weight of the composition. In some embodiments, the composition comprises glycerin, optionally wherein glycerin is present in an amount of from 10% to 40%, from 15% to 30%, from 15% to 25%, or about 20% by weight of the composition. In some embodiments, the composition comprises sorbitol, optionally wherein sorbitol is present in an amount of from 10% to 40%, from 15% to 30%, from 15% to 25%, or about 20% by weight of the composition.

In some embodiments, the oral care compositions of the present invention may comprise polyethylene glycol (PEG) of various weight percentages of the composition as well as various ranges of average molecular weights. The PEG may have a range of average molecular weight from 100 Daltons to 1600 Daltons, preferably from 200 to 1000, from 400 to 800, from 500 to 700 Daltons, or a combination thereof. In some embodiments, the polyethylene glycol is PEG 600. In some embodiment, the PEG, e.g., PEG 600, is present in an amount of less than or equal to 1%, from 0.01% to 1%, or from 0.1% to 1% by weight of the composition.

The oral care compositions of the present invention may include a preservative. Suitable preservatives include, but are not limited to, sodium benzoate, potassium sorbate, methylisothiazolinone, paraben preservatives, for example methyl p-hydroxybenzoate, propyl p-hydroxybenzoate, and mixtures thereof.

The oral care compositions of the present invention may include a sweetener such as, for example, saccharin, for example sodium saccharin, acesulfam, neotame, cyclamate or sucralose; natural high-intensity sweeteners such as thaumatin, stevioside or glycyrrhizin; or such as sorbitol, xylitol, maltitol or mannitol. One or more of such sweeteners may be present in an amount of from 0.005% to 5% by weight, for example 0.01% to 1%, for example 0.01% to 0.5%, by weight of the composition.

The oral care compositions of the present invention may include a flavoring agent. Suitable flavoring agents include, but are not limited to, essential oils and various flavoring aldehydes, esters, alcohols, and similar materials, as well as sweeteners such as sodium saccharin. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. The flavoring agent is typically incorporated in the oral composition at a concentration of 0.01 to 3% by weight.

The oral care composition of the invention may include one or more pH modifying agents. For example, the oral care composition may include one or more acidifying agents and/or one or more basifying agents configured to reduce and/or increase the pH thereof, respectively. Illustrative acidifying agents and/or one or more basifying agents may be or include, but are not limited to, an alkali metal hydroxide, such as sodium hydroxide and/or potassium hydroxide, citric acid, hydrochloric acid, or the like, or combinations thereof.

The oral care composition of the invention may also include one or more buffering agents configured to control or modulate the pH within a predetermined or desired range. Illustrative buffering agents may include, but are not limited to, sodium bicarbonate, sodium phosphate, sodium carbonate, sodium acid pyrophosphate, sodium citrate, and mixtures thereof. Sodium phosphate may include monosodium phosphate ($NaH_2PO_4$), disodium phosphate ($Na_2HPO_4$), trisodium phosphate ($Na_3PO_4$), and mixtures thereof. In a typical embodiment, the buffering agent may be anhydrous sodium phosphate dibasic or disodium phosphate and/or sodium phosphate monobasic. In another embodiment, the buffering agent includes anhydrous sodium phosphate dibasic or disodium phosphate, and phosphoric acid (e.g., syrupy phosphoric acid; 85%-Food Grade).

The oral care composition of the invention may include anticalculus agents. Illustrative anticalculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments, the anticalculus agent includes tetrasodium pyrophosphate (TSPP), sodium tripolyphosphate (STPP), or a combination thereof.

The oral care composition of the invention may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, or the like, or combinations and mixtures thereof.

The oral care composition of the invention may include one or more pigments, such as whitening pigments. In some embodiments, the whitening pigments include particles ranging in size from about 0.1 µm to about 10 µm with a refractive index greater than about 1.2. Suitable whitening agents include, without limitation, titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxyapatite particles, calcium carbonate particles, zinc phosphate particles, silicon dioxide particles, zirconium silicate particles, or the like, or mixtures and combinations thereof. The whitening pigment, such as titanium dioxide particles, may be present in an amount that is sufficient to whiten the teeth.

All ingredients for use in the compositions described herein should be orally acceptable. As used herein, "orally acceptable" may refer any ingredient that is present in a composition as described in an amount and form which does not render the composition unsafe for use in the oral cavity.

In another aspect, the present invention provides a method to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity, comprising applying an effective amount of any of oral care compositions as disclosed herein to the oral cavity of a subject in need thereof. The method may include contacting the oral care composition with water. The method may also include contacting the surface of the teeth with the oral care composition. Contacting the surface of the teeth with the oral care composition may include disposing the oral care composition (e.g., toothpaste) on a toothbrush and brushing the teeth with the toothbrush. The oral care composition may be applied and/or contacted with the surfaces of the teeth at predetermined intervals. For example, a daily basis, at least once a day, twice a day, or more, for multiple days, or alternatively every other day. In another example, the oral care composition may be applied and/or contacted with the surfaces of the teeth at least once a day, at least once every two days, at least once every three days, at least once every five days, at least once a week, at least once every two weeks, or at least once a month. The oral care composition thereof may be utilized for up to 2 weeks, up to 3 weeks, up to 4 weeks, up to 6 weeks, up to 8 weeks, or greater.

In another aspect, the invention provides the use of any of oral care compositions as disclosed herein to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, or (xi) clean teeth and oral cavity, in a subject in need thereof.

In another aspect, the invention provides the use of a thickening system comprising xanthan gum and a synthetic polyacrylic acid polymer in the manufacture of an oral care composition, e.g., toothpaste or gel, comprising a calcium carbonate, wherein the calcium carbonate is present in an amount of from 25% to 40% by weight of the composition, wherein xanthan gum is present in an amount of 0.2% to 0.5% by weight of the composition, and wherein the synthetic polyacrylic acid polymer is present in an amount of from 0.2% to 0.5% by weight of the composition. In some embodiments, the calcium carbonate is natural calcium carbonate, precipitated calcium carbonate or a combination thereof. In some embodiments, the calcium carbonate is precipitated calcium carbonate. In some embodiments, the calcium carbonate is present in an amount of from 25% to 35%, from 30% to 40%, from 35% to 40%, from 30% to 35%, from 32% to 38%, from 33% to 37%, from 34% to 36%, or about 35% by weight of the composition. In some embodiments, the synthetic polyacrylic acid polymer is a carbomer. In some embodiments, the synthetic polyacrylic acid polymer is Carbopol® 956 or Carbopol® ETD2020. In some embodiments, the synthetic polyacrylic acid polymer is Carbopol® 956. In some embodiments, the synthetic polyacrylic acid polymer is Carbopol® ETD2020. In some embodiments, the synthetic polyacrylic acid polymer is a combination of Carbopol® 956 and Carbopol® ETD2020. In some embodiments, the synthetic polyacrylic acid polymer is present in an amount of from 0.2% to 0.4%, from 0.3% to 0.5%, from 0.35% to 0.45%, e.g., about 0.3% or about 0.4%, by weight of the composition. In some embodiments, xanthan gum is present in an amount of 0 from 0.2% to 0.4%, from 0.3% to 0.5%, from 0.35% to 0.45%, e.g., about 0.3% or about 0.4%, by weight of the composition.

EXAMPLES

Example 1

Two PCC (precipitated calcium carbonate)-based toothpastes of the invention (Compositions I and II) and a standard PCC toothpaste (Comparative Composition I) were prepared as indicated in Table 1.

TABLE 1

| Ingredient | Composition I (wt. %) | Composition II (wt. %) | Comparative Composition I (wt. %) |
|---|---|---|---|
| Water | 34.54 | 34.54 | 34.45 |
| Glycerin | 20 | 20 | 16 |
| Tetrasodium pyrophosphate | 0.6 | 0.6 | 0.5 |
| Sodium monofluorophosphate | 1.1 | 1.1 | 1.1 |
| Sodium bicarbonate | 0.4 | 0.4 | 0.5 |
| Precipitated calcium carbonate | 35 | 35 | 40 |
| Benzyl alcohol | 0.4 | 0.4 | 0.3 |
| 35% sodium lauryl sulfate | 4.64 | 4.64 | 5.03 |
| Betaine | 1.25 | 1.25 | 0 |
| Xanthan gum | 0.4 | 0.4 | 0 |
| Carbopol ® 956 | 0.4 | 0.2 | 0 |
| Carbopol ® ETD 2020 | 0 | 0.2 | 0 |
| Sodium CMC | 0 | 0 | 0.85 |
| Flavor, sweetener, preservative and colors | Balance | Balance | Balance |

The three toothpastes differ in type of thickeners present. Compositions I and II contains 0.4% xanthan gum and 0.4% synthetic polyacrylic acid polymer (0.4% Carbopol® 956 (Composition I) or 0.2% Carbopol® 956 and 0.2% Carbopol® ETD 2020 (Composition II)), while Comparative Composition I contains 0.85% sodium CMC, no Carbopol, and no xanthan gum.

The rheological properties of Compositions I and II were compared with Comparative Composition I. Viscosity and dynamic yield stress of the toothpastes were monitored at room temperature over time up to four weeks as indicated in Table 2. The rheological properties were measured at room temperature by Brookfield viscometer using the V74 spindle flow method, equipped with Fitflow software. Dynamic yield stress was calculated using Fitflow software. The results are shown in Table 2.

TABLE 2

Rheological properties monitored at RT over time

| | Composition I | | Composition II | | Comparative composition I | |
|---|---|---|---|---|---|---|
| | Viscosity (cps) | Dynamic yield stress (Pa) | Viscosity (cps) | Dynamic yield stress (Pa) | Viscosity (cps) | Dynamic yield stress (Pa) |
| Initial | 290815 | 62.5 | 483081 | 107 | 230269 | 30.2 |
| 2 hours | 399669 | 83 | 739759 | 184 | 275163 | 32.5 |
| 1 day | 557669 | 129 | 816150 | 199 | 302409 | 33.2 |
| 1 week | 686298 | 171 | 893379 | 227 | 356385 | 43.4 |
| 3 weeks | 563337 | 119 | 965390 | 208 | 346724 | 44.6 |
| 4 weeks | 681274 | 151 | 963264 | 238 | 414419 | 53.7 |

As shown in Table 2, Compositions I and II maintained their viscosity and dynamic yield stress within the desired ranges (viscosity range: 200000-1000000 cps and dynamic yield stress range: 60-250 Pa) over time. When compared to a standard PCC formulation containing 0.8% carboxymethylcellulose (CMC), no Carbopol, and no xanthan gum (Comparative Composition I), the main difference was observed in the dynamic yield stress range. The dynamic yield stress range of Comparative Composition I was within 30-60 Pa, which may present a lower standup of the formulation. This result shows that Carbopol provides unique rheological properties, especially when combined with xanthan gum.

Example 2

Toothpaste formulations useful in the invention are prepared using the ingredients shown in Table 3.

TABLE 3

| Ingredient | wt. % |
| --- | --- |
| Water | 20-55 |
| Humectant | 15-30 |
| Sweetener | 0.1-0.5 |
| Synthetic polyacrylic acid polymer | 0.2-0.5 |
| Xanthan gum | 0.2-0.5 |
| Sodium monofluorophosphate | 1.1 |
| Tetrasodium pyrophosphate | 0.3-0.6 |
| Precipitated calcium carbonate (PCC) | 25-40 |
| sodium lauryl sulfate (35% sol.) | 1-6 |
| Polyethylene glycol | 0 or 0.01-1 |
| Betaine (30% sol.) | 0.75-2 |
| Benzyl alcohol | 0.2-0.5 |
| flavor | 0.5-2 |
| colorants | 0.0001-0.005 |
| Additives (pH stabilizers, salts) | 0.5-2 |
| Total | 100 |

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

The invention claimed is:

1. An oral care composition comprising precipitated calcium carbonate and a thickening system consisting of xanthan gum and a carbomer, wherein the precipitated calcium carbonate is present in an amount of from 30% to 40% by weight of the composition, wherein xanthan gum is present in an amount of 0.3% to 0.5% by weight of the composition, and wherein the carbomer is present in an amount of from 0.2% to 0.5% by weight of the composition;
wherein the oral care composition exhibits a viscosity of 200,000-1,000,000 cps and a dynamic yield stress of 60-250 Pa.

2. The composition of claim 1, wherein the composition comprises a humectant selected from glycerin and sorbitol.

3. The composition of claim 1, wherein the composition comprises a fluoride ion source.

4. The composition of claim 1, wherein the composition comprises a zinc ion source.

5. The composition of claim 1, wherein the composition comprises a basic amino acid, in free or salt from.

6. The composition of claim 1, wherein the composition comprises:
about 0.4 wt. % carbomer
about 0.4 wt. % xanthan gum,
about 20 wt. % glycerin, and
about 35 wt. % precipitated calcium carbonate (PCC).

7. The composition of claim 1, wherein the composition comprises a polyethylene glycol in amount of less than or equal to 1% by weight of the composition.

8. The composition of claim 1, wherein the composition is a toothpaste or gel.

9. The composition of claim 1 for use in (i) reducing or inhibiting formation of dental caries, (ii) reducing, repairing or inhibiting pre-carious lesions of the enamel, (iii) reducing or inhibiting demineralization and promote remineralization of the teeth, (iv) reducing hypersensitivity of the teeth, (v) reducing or inhibiting gingivitis, (vi) promoting healing of sores or cuts in the oral cavity, (vii) reducing levels of acid producing bacteria, (viii) reducing or inhibiting microbial biofilm formation in the oral cavity, (ix) reducing or inhibiting plaque formation in the oral cavity, (x) promoting systemic health, or (xi) cleaning teeth and oral cavity.

* * * * *